US010448896B2

United States Patent
Kang (10) Patent No.: US 10,448,896 B2
(45) Date of Patent: Oct. 22, 2019

(54) METHOD AND APPARATUS FOR PROCESSING BIO-SIGNALS USING RECURSIVE ESTIMATION

(71) Applicant: SAMSUNG ELECTRONICS CO., LTD., Suwon-si (KR)

(72) Inventor: Jaemin Kang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 456 days.

(21) Appl. No.: 14/577,150

(22) Filed: Dec. 19, 2014

(65) Prior Publication Data

US 2016/0007926 A1  Jan. 14, 2016

(30) Foreign Application Priority Data

Jul. 14, 2014 (KR) ........................ 10-2014-0088457

(51) Int. Cl.
*A61B 5/00* (2006.01)
*A61B 5/0402* (2006.01)
*A61B 5/11* (2006.01)
*A61B 5/04* (2006.01)
*A61B 5/0476* (2006.01)
*A61B 5/0488* (2006.01)

(52) U.S. Cl.
CPC ............ *A61B 5/721* (2013.01); *A61B 5/0402* (2013.01); *A61B 5/11* (2013.01); *A61B 5/681* (2013.01); *A61B 5/0002* (2013.01); *A61B 5/0059* (2013.01); *A61B 5/04012* (2013.01); *A61B 5/0476* (2013.01); *A61B 5/0488* (2013.01); *A61B 5/1102* (2013.01)

(58) Field of Classification Search
CPC ..... A61B 5/11; A61B 5/0402; A61B 5/04012; A61B 5/7207; A61B 5/72–7235; A61B 5/721; G06K 9/00496; G06K 9/0051
See application file for complete search history.

(56) References Cited

U.S. PATENT DOCUMENTS 5,738,104 A * 4/1998 Lo ...................... A61B 5/02438
600/509
8,073,516 B2 12/2011 Scharf et al.
9,788,794 B2 * 10/2017 LeBoeuf .............. A61B 5/7235
(Continued)

FOREIGN PATENT DOCUMENTS

JP          11-9564 A      1/1999
KR      10-0462182 B1    12/2004
(Continued)

OTHER PUBLICATIONS

Fukushima et al., "Estimating Hear Rate using Wrist-type Photoplethysmography and Acceleration sensor while running", Sep. 1, 2012, 34th Int. Conf. of the IEEE EMBS, San Diego, California, USA, 2901-2904.*

*Primary Examiner* — Lynsey C Eiseman
*Assistant Examiner* — Jonathan Kuo
(74) *Attorney, Agent, or Firm* — Sughrue Mion, PLLC (57) ABSTRACT

A method of processing a bio-signal includes: generating a motion pattern from a motion of an object body; estimating a next point in time of a motion occurrence from the motion pattern; and generating a bio-signal pattern by combining an attenuation factor with a bio-signal of the object body at the estimated next point in time of the motion occurrence.

18 Claims, 6 Drawing Sheets

(56) References Cited

U.S. PATENT DOCUMENTS

2010/0292589 A1* 11/2010 Goodman .............. A61B 5/021
                                                              600/500
2011/0098583 A1    4/2011 Pandia et al.
2015/0006446 A1*  1/2015 Chiba .................. A61B 5/1123
                                                              706/12

FOREIGN PATENT DOCUMENTS

| KR | 10-2008-0069392 A | 7/2008 | | |
|----|-------------------|--------|---|---|
| KR | 10-2013-0092849 A | 8/2013 | | |
| KR | 10-1301304 B1 | 8/2013 | | |
| WO | WO2013128972 | * | 6/2013 | ............... A61B 5/11 |

* cited by examiner

SECTION A    SECTION B

FIG. 8B

SECTION A

FIG. 8C

SECTION B

• R PEAK
▼ MOTION ARTIFACT

FIG. 9

METHOD AND APPARATUS FOR PROCESSING BIO-SIGNALS USING RECURSIVE ESTIMATION

CROSS-REFERENCE TO RELATED APPLICATION

This application claims priority from Korean Patent Application No. 10-2014-0088457, filed on Jul. 14, 2014, in the Korean Intellectual Property Office, the disclosure of which is incorporated herein in its entirety by reference.

BACKGROUND

1. Field

Apparatuses and methods consistent with exemplary embodiments relate to processing bio-signals using recursive estimation.

2. Description of the Related Art

Recently, since various bio-signals can be measured in a daily life, accuracy and convenience of diagnosis are increased. Also, a smart healthcare system may be used to provide health-related services by using a database of an individual's health information, assist medical teams with remote diagnosis, and deliver the diagnosis results and/or prescription to patients.

A human body may be modeled as a volume conductor in which an electric field is formed by an action potential generated according to an electrical excitation of cells. Thus, electrical properties of the human body may be measured by detecting a slight amount of currents from the human body, or by detecting a change in an amount of currents with respect to external stimulus.

Generally, an electrocardiogram (ECG), an electromyography (EMG), an electroencephalogram (EEG), an electrooculogram (EOG), a pulse, a blood pressure, etc. may be measured by using the above principles.

When the measurement of the bio-signals is performed in an individual's daily life, a motion artifact may be mingled in the bio-signals due to an individual's motion. Thus, apparatuses and methods for decreasing the motion artifact are needed.

SUMMARY

Exemplary embodiments may address at least the above problems and/or disadvantages and other disadvantages not described above. The exemplary embodiments are not required to overcome the disadvantages described above, and may not overcome any of the problems described above.

One or more exemplary embodiments provide a method and an apparatus for measuring a bio-signal having higher reliability by decreasing a motion artifact of the bio-signal.

One or more exemplary embodiments also provide a method and an apparatus for measuring a bio-signal, regardless of an individual's motion, by decreasing a motion artifact of the bio-signal.

Additional aspects will be set forth in part in the description which follows and, in part, will be apparent from the description, or may be learned by practice of the presented exemplary embodiments.

According to an aspect of an exemplary embodiment, a method of processing a bio-signal includes: generating a motion pattern from motion of an object body; estimating a next point in time of motion occurrence from the motion pattern; and generating a bio-signal pattern by combining an attenuation factor attenuating motion to a bio-signal of the object body, at the next point in time of motion occurrence.

The next point in time of motion occurrence may be estimated by using at least one motion peak cycle included in the motion pattern.

The next point in time of motion occurrence may be a most recent point in time of motion occurrence, to which a most recent motion peak cycle is added.

The next point in time of motion occurrence may be a most recent point in time of motion occurrence, to which an average of the at least one motion peak cycle is added.

The next point in time of motion occurrence may be a most recent point in time of motion occurrence, to which a value of the at least one motion peak cycle which is adaptively filtered is added.

The attenuation factor may be a signal smaller than 1, when 1 is a reference value.

A size of the attenuation factor may be 0 to less than 1.

A width of the attenuation factor may be determined by using at least one section of motion occurrence included in the motion pattern.

The method may further include estimating a next point in time of peak occurrence of the bio-signal from a previous bio-signal pattern. The generating of the bio-signal pattern may include combining a reinforcement factor reinforcing the bio-signal to the bio-signal of the object body, which is of the next point in time of peak occurrence.

The next point in time of peak occurrence may be estimated by using at least one signal peak cycle included in the previous bio-signal pattern.

The next point in time of peak occurrence may be a most recent point in time of peak occurrence, to which a most recent signal peak cycle is added.

The next point in time of peak occurrence may be a most recent point of peak occurrence, to which a value of the at least one signal peak cycle which is adaptively filtered is added.

The reinforcement factor may be a signal larger than 1, when 1 is a reference value.

A width of the reinforcement factor may be determined by using at least one section of peak occurrence included in the previous bio-signal pattern.

The bio-signal may be an electrocardiogram (ECG) signal.

According to an aspect of an exemplary embodiment, a method of processing a bio-signal includes: generating a bio-signal pattern from the bio-signal of an object body; estimating a next point in time of peak occurrence of the bio-signal from the bio-signal pattern; and generating a new bio-signal pattern by combining a reinforcement factor reinforcing a new bio-signal to the new bio-signal of the next point in time of peak occurrence.

According to an aspect of an exemplary embodiment, an apparatus for processing a bio-signal includes: a communication module receiving at least one of a motion signal of an object body and the bio-signal of the object body; and a processor generating a motion pattern from the motion signal, estimating a next point in time of motion occurrence from the motion pattern, and generating a bio-signal pattern by combining an attenuation factor attenuating motion to the bio-signal of the next point in time of motion occurrence.

The processor may estimate the next point in time of motion occurrence by using a motion peak cycle included in the motion pattern.

The processor may estimate a next point in time of peak occurrence of the bio-signal from a previous bio-signal pattern, and combine a reinforcement factor reinforcing the bio-signal to the bio-signal of the next point in time of peak occurrence, to generate the bio-signal pattern.

The processor may estimate the next point in time of peak occurrence by using a signal peak cycle of the bio-signal, included in the previous bio-signal pattern.

BRIEF DESCRIPTION OF THE DRAWINGS

The above and/or other aspects will become more apparent by describing certain exemplary embodiments with reference to the accompanying drawings, in which.

DETAILED DESCRIPTION

Certain exemplary embodiments are described in greater detail below with reference to the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects of the present description. Sizes of elements in the drawings may be exaggerated for convenience of explanation. In other words, since sizes and thicknesses of components in the drawings are arbitrarily illustrated for convenience of explanation, the following exemplary embodiments are not limited thereto.

In this specification, "an object body" denotes an object from which a bio-signal is to be measured. Here, the object may be a human, an animal, or a part of the human or the animal. "A bio-signal" is a unique signal generated from the object body. For example, an electrocardiogram (ECG), a ballistocardiogram (BCG), a photoplethysmograph (PPG), a brain wave, an electromyogram, etc. may be included in the bio-signal. Also, when measuring a bio-signal of the object body, "a motion artifact" may be a noise generated by a half cell potential and a change of impedance between the object body and a measuring electrode, due to predetermined motion of the object body.

Figure 1:
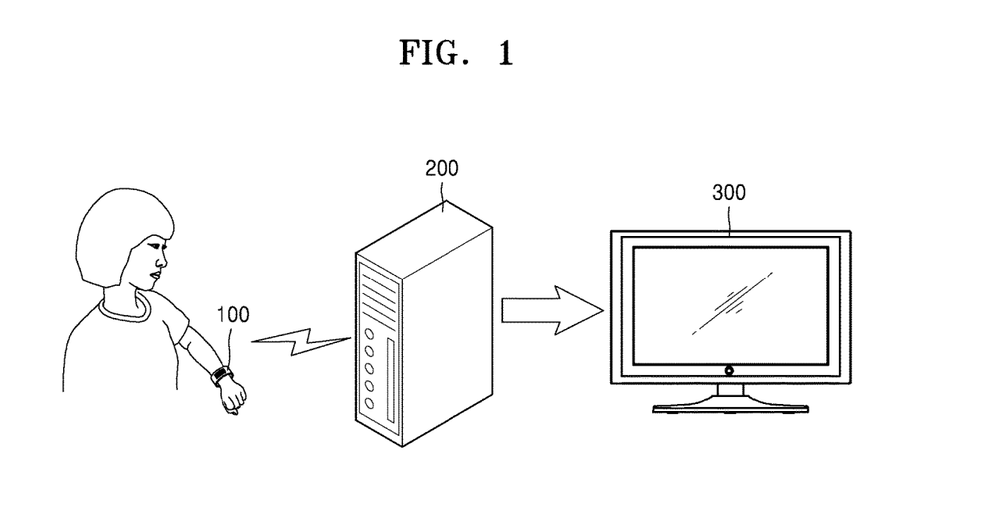
FIG. 1 is a schematic view of a bio-signal processing system according to an exemplary embodiment.
Figure 2:
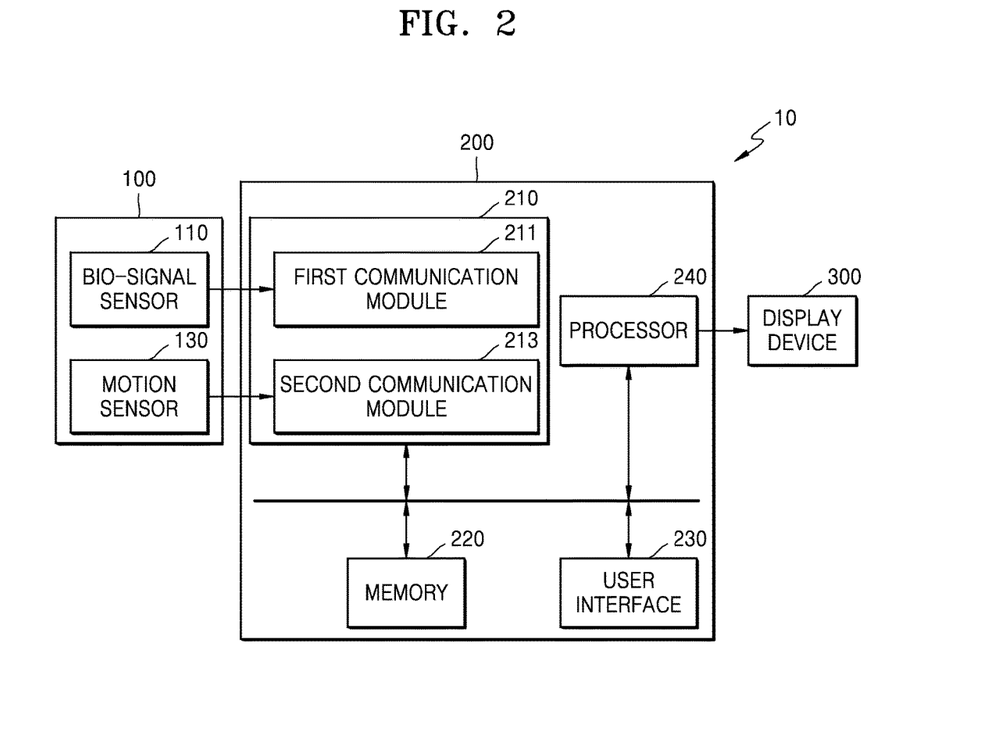
FIG. 2 is a block diagram of a bio-signal processing system according to an exemplary embodiment.

FIG. 1 is a schematic view of a bio-signal processing system 10 according to an exemplary embodiment. FIG. 2 is a block diagram of the bio-signal processing system 10. Referring to FIGS. 1 and 2, the bio-signal processing system 10 may include a measuring device 100 measuring at least one of a bio-signal and motion of an object body, a processing device 200 processing the bio-signal by using the at least one of the bio-signal and the motion received from the measuring device 100, and a display device 300 displaying the processed bio-signal. The measuring device 100, the processing device 200, and the display device 300 may be realized as a single device. Alternatively, two of the measuring device 100, the processing device 200, and the display device 300 may be realized as a single device and the rest one may be realized as a separate device. Of course, each of the measuring device 100, the processing device 200, and the display device 300 may be realized as a separate device. In addition, at least a part of the processing device 200 may be included in the measuring device 100 or in the display device 300. When the bio-signal processing system 10 includes a plurality of devices, the plurality of devices may be connected to one another by wires or wirelessly.

The measuring device 100 may include a bio-signal sensor 110 detecting a bio-signal of an object body and a motion sensor 130 detecting motion of the object body. The measuring device 100 may be a portable device, for example, a wearable device. For example, the measuring device 100 may be worn on a wrist, a chest, and an ankle of the object body.

The bio-signal sensor 110 is a sensor detecting the bio-signal of the object body, such as an electrocardiography (ECG), a galvanic skin reflex (GSR), and a pulse wave. The bio-signal sensor 110 may include a plurality of electrodes. The plurality of electrodes may contact the object body when the measuring device 100 is worn on the object body.

The motion sensor 130 is a sensor detecting the motion of the object body. The motion sensor 130 may include an acceleration sensor, a gyro sensor, and a terrestrial magnetic sensor. In addition, sensors which may recognize motion of the object body may be used as the motion sensor 130.

Although FIG. 2 illustrates that the bio-signal sensor 110 and the motion sensor 130 are embodied in a single device, e.g., the measuring device 100, exemplary embodiments are not limited thereto. For example, the bio-signal sensor 110 and the motion sensor 130 may be separate devices. Also, according to still another exemplary embodiment, the motion sensor 130 may be omitted.

The processing device 200 may include a communication module 210, i.e., a communicator, receiving at least one of the bio-signal and a motion signal from the measuring device 100, a memory 220 in which various data for processing the at least one of the bio-signal and the motion signal is stored, a user interface 230 which may receive an input of a user command, and a processor 240 processing the bio-signal. Other components may further be included in addition to the illustrated components. Also, one or more of the illustrated components may be omitted.

The communication module 210 may include a first communication module 211 receiving the bio-signal from the bio-signal sensor 110 and a second communication module 213 receiving the motion signal from the motion sensor 130. The first communication module 211 and the second communication module 213 may provide interfaces for direct or indirect connection with the bio-signal sensor 110 and the motion sensor 130, respectively. The communication module 210 may transmit and receive data to and from the measuring device 100 via a wire or wireless network or via wired serial communication.

The memory 220 may store data generated during an operation of the bio-signal processing system 10. According to an exemplary embodiment, the memory 220 is a storage medium, and a person of ordinary skill in the art will understand that the memory 220 may include a hard disk drive (HDD), a read only memory (ROM), a random access memory (RAM), a flash memory, and/or a memory card.

The user interface 230 may receive an input for manipulating the processing device 200 from the user or may output a bio-signal pattern processed by the processing device 200. The user interface 230 may include, for example, a button, a key pad, a switch, a dial, or a touch interface for the user to directly manipulate the processing device 200. The user interface 230 may include a display unit for displaying an image and be realized as a touch screen. According to another exemplary embodiment, the user interface 230 may include an input/output (I/O) port for connecting human interface devices (HID). The user interface 230 may include an I/O port for an input and/or output of the image.

The processor 240 generates the bio-signal pattern by using at least one of the bio-signal and the motion signal. A method of generating the bio-signal pattern will be described later.

The display device 300 displays the bio-signal processed by the processing device 200. For example, the display device 300 may include different types of output devices, such as a display panel, a liquid crystal display (LCD) screen, and a monitor which may be provided in the bio-signal processing system 10.

However, the bio-signal processing system 10 according to an exemplary embodiment may omit the display device 300, and the communication module 210 may output the bio-signal processed by the processing device 200 via an external display device (not shown).

Figure 3:
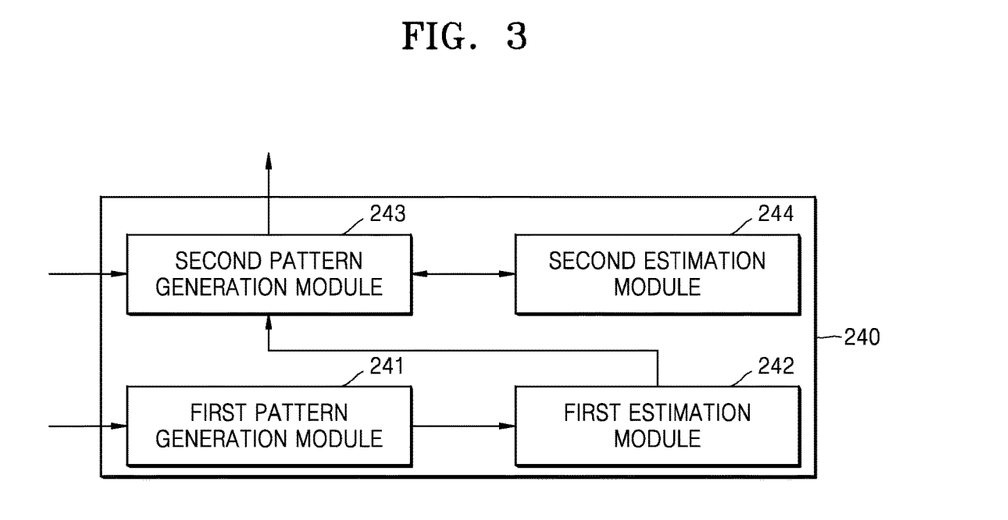
FIG. 3 is a block diagram illustrating the processor of FIG. 2.

FIG. 3 is a block diagram illustrating a configuration of the processor 240 of FIG. 2. As illustrated in FIG. 3, the processor 240 may include a first pattern generation module 241 generating a motion pattern by using results received from the motion sensor 130, a first estimation module 242 estimating a next point in time of motion occurrence from the motion pattern, a second pattern generation module 243 generating the bio-signal pattern by using results received from the bio-signal sensor 110, and a second estimation module 244 estimating a next peak point in time of the bio-signal from the bio-signal pattern.

The first pattern generation module 241 may generate the motion pattern from the motion signal received from the motion sensor 130. For example, the first pattern generation module 241 may calculate a size of a vector of X, Y, and Z factors from the motion signal and may filter the size of the vector which is calculated by using a bandpass filter. Also, the first pattern generation module 241 may detect motion peaks by using the filtered signal and generate the motion pattern by adaptively filtering the detected motion peaks. The motion peak may be a signal which may be generated when motion occurs. The motion pattern may include irregular motion occurrences or temporary motion occurrences, in addition to regular motion occurrences.

Figure 4:
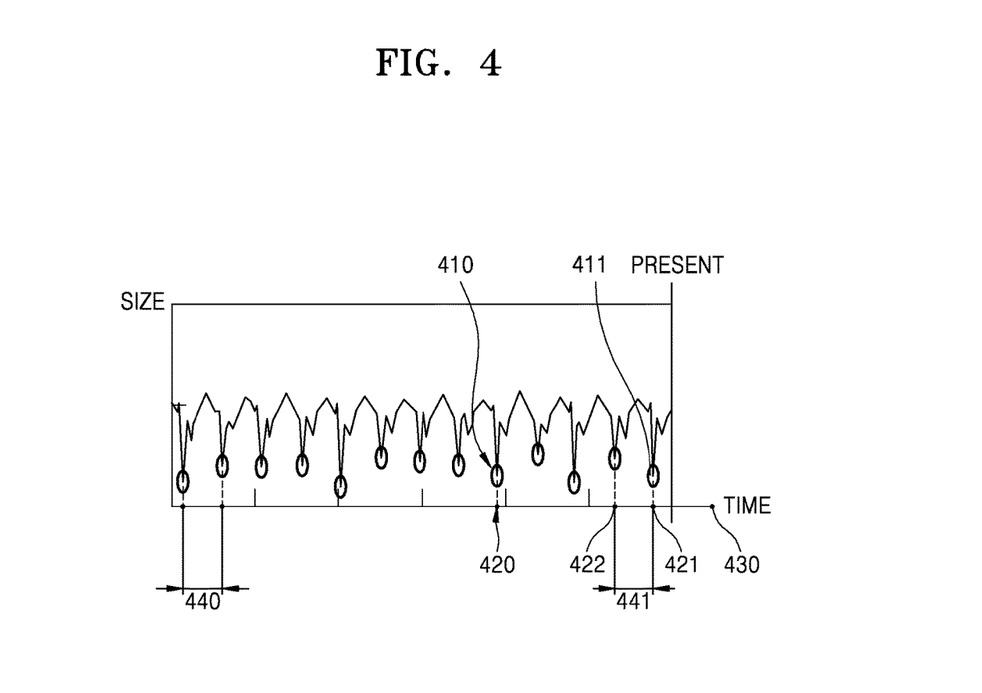
FIG. 4 shows an example of a motion pattern according to an exemplary embodiment.

The first estimation module 242 may estimate the next point in time of motion occurrence from the motion pattern. FIG. 4 shows an example of a motion pattern according to an exemplary embodiment. Referring to FIG. 4, the motion pattern may include at least one motion peak 410 or 411. The motion pattern is generated based on a motion signal previously generated, and thus, the motion peak 410 included in the motion pattern may include information about points in time (e.g., a point in time 420) of motion occurrence. A point in time of motion occurrence which is the most recent may be referred to as a most recent point in time 421 of motion occurrence. Also, a point in time of motion occurrence which is to be first after the most recent point in time 421 of motion occurrence may be referred to as a next point in time 430 of motion occurrence. Moreover, a time interval between neighboring points of motion occurrence may be referred to as a motion peak cycle 440. In particular, a motion peak cycle between the most recent point in time 421 of motion occurrence and a point in time 422 of motion occurrence which neighbors the most recent point in time 421 of motion occurrence may be referred to as a most recent motion peak cycle 441.

The first estimation module 242 may estimate the next point in time 430 of motion occurrence by using the motion peak cycle 440 included in the motion pattern. For example, the first estimation module 242 may estimate the next point in time 430 of motion occurrence based on the most recent point in time 421 of motion occurrence, to which the most recent motion peak cycle 441 is added. Alternatively, the first estimation module 242 may estimate the next point in time 430 of motion occurrence based on the most recent point in time 421 of motion occurrence, to which an average of at least one motion peak cycle 440 included in the motion pattern is added. In addition, the first estimation module 242 may estimate the next point in time 430 of motion occurrence based on the most recent point in time 421 of motion occurrence, to which a value of the at least one motion peak cycle 440 which is adaptively filtered is added. Furthermore, the first estimation module 242 may estimate the next point in time 430 of motion occurrence by using various other methods.

The second pattern generation module 243 may generate the bio-signal pattern by using the results received from the bio-signal sensor 110. For example, the second pattern generation module 243 may amplify the bio-signal, for example, an ECG signal, and may filter the amplified ECG signal by using a finite impulse response (FIR) bandpass filter. Also, the second pattern generation module 243 may detect peaks in the filtered ECG signal and adaptively filter the detected peaks to generate the bio-signal pattern. A signal peak in the bio-signal is a signal generated when a specific organ of an object is in a specific state. For example, an R peak in an ECG wave form may be a signal which may be generated when a ventricle contracts. The bio-signal, particularly, the bio-signal of a heart, may generally have a periodic wave form, and thus, the bio-signal pattern may be a pattern in which a periodic signal is repeated.

Figure 5:
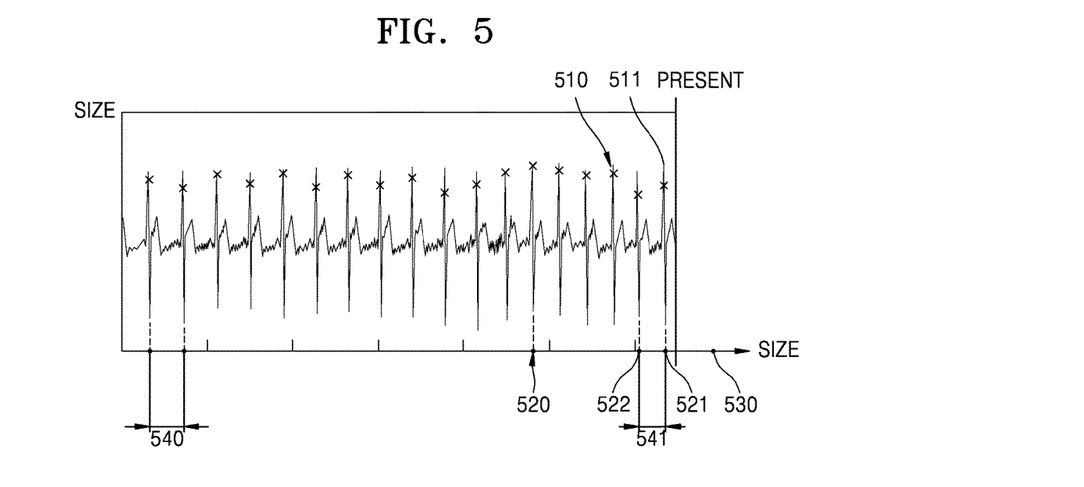
FIG. 5 shows an example of a bio-signal pattern according to an exemplary embodiment.

The second estimation module 244 may estimate the next point in time of peak occurrence of the bio-signal from the bio-signal pattern. FIG. 5 shows an example of a bio-signal pattern according to an exemplary embodiment. Referring to FIG. 5, the bio-signal pattern may include at least one signal peak 510.

The bio-signal pattern is generated based on a bio-signal previously generated, and thus, the signal peak 510 included in the bio-signal pattern may include information about points in time (e.g., a point in time 520) of signal peak occurrence. A point in time of peak occurrence which is the most recent may be referred to as a most recent point in time 521 of peak occurrence 511. Also, a point in time of peak occurrence which is to be first after the most recent point in time 521 of peak occurrence may be referred to as a next point in time 530 of peak occurrence. Moreover, a time interval between neighboring points of peak occurrence may be referred to as a signal peak cycle 540. In particular, a signal peak cycle between the most recent point in time 521 of peak occurrence and a point in time 522 of peak occurrence which neighbors the most recent point in time 521 of peak occurrence may be referred to as a most recent signal peak cycle 541.

The second estimation module 244 may estimate the next point in time 530 of peak occurrence by using the signal peak cycle 540 included in the bio-signal pattern. For example, the second estimation module 244 may estimate the next point in time 530 of peak occurrence based on the most recent point in time 521 of peak occurrence, to which the most recent signal peak cycle 541 is added. Alternatively, the second estimation module 244 may estimate the next point in time 530 of peak occurrence as the most recent point in time 521 of peak occurrence, to which an average of at least one signal peak cycle 540 included in the bio-signal pattern is added. In addition, the second estimation module 244 may estimate the next point in time 530 of peak occurrence as the most recent point in time 521 of peak occurrence, to which a value of the at least one signal peak cycle 540 which is adaptively filtered is added. Furthermore, the second estimation module 244 may estimate the next point in time 530 of peak occurrence by using various other methods.

To generate the bio-signal pattern from the bio-signal, the second pattern generation module 243 may use at least one of an attenuation factor for attenuating motion and a reinforcement factor for reinforcing the bio-signal.

The attenuation factor may be a factor which attenuates the motion signal of the object body. For example, the attenuation factor may be a signal smaller than a reference value. When the reference value is 1, a size of the attenuation signal may be 0 to less than 1. Also, a width of the attenuation factor may be determined by using at least one section of motion occurrence included in the motion pattern. For example, the width of the attenuation factor may be equal to or smaller than the section of motion occurrence. The width and size of the attenuation factor may vary according to motion patterns of object bodies, or may have predetermined values.

The reinforcement factor may be a factor which reinforces the bio-signal of the object body. For example, the reinforcement factor may be a signal larger than the reference value. When the reference value is 1, a size of the reinforcement signal may be equal to or larger than, for example, 1.5. Also, a width of the reinforcement factor may be determined by using at least one section of peak occurrence included in the bio-signal pattern. For example, the width of the reinforcement factor may be equal to or smaller than the section of peak occurrence. The width and size of the reinforcement factor may vary according to bio-signals of object bodies, or may have predetermined values.

As described above, the second pattern generation module 243 may use at least one of the attenuation factor and the reinforcement factor to generate the bio-signal pattern. For example, to generate a new bio-signal pattern based on a new received bio-signal, the second pattern generation module 243 may combine the attenuation factor with the bio-signal at a next point in time of motion occurrence or may combine the reinforcement factor with the bio-signal at a next point in time of peak occurrence. In the bio-signal pattern generated by combining the attenuation factor with the bio-signal, the motion signal appears to be lower. Thus, motion artifacts are decreased. Also, the bio-signal pattern generated by combining the reinforcement factor with the bio-signal results in a reinforced bio-signal. Thus, it becomes easy to identify the bio-signal, and thus, the effect of the motion artifacts is relatively decreased or substantially eliminated.

Figure 6:
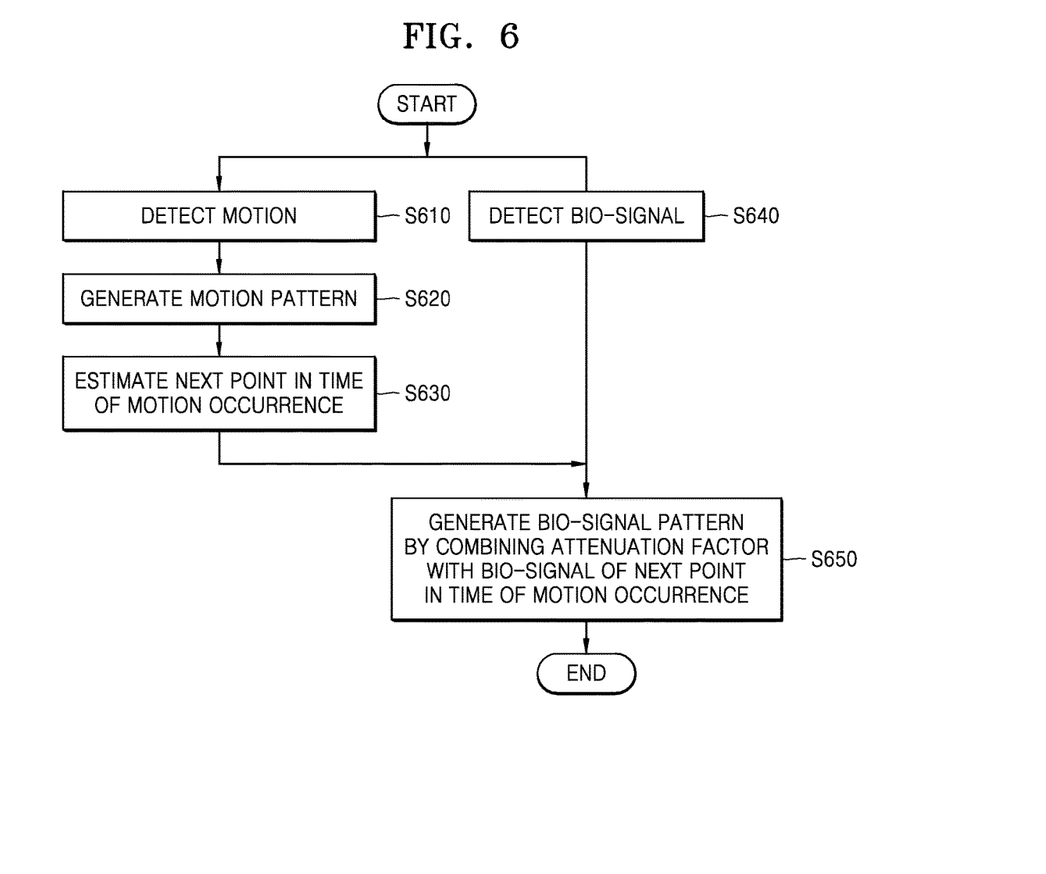
FIG. 6 is a flowchart illustrating a method of decreasing a motion artifact according to an exemplary embodiment.

FIG. 6 is a flowchart illustrating a method of decreasing a motion artifact, according to an exemplary embodiment. First, the motion sensor 130 detects motion of an object body in operation S610. The motion sensor 130 may be an acceleration sensor, but exemplary embodiments are not limited thereto. A motion signal which is detected is applied to the processing device 200.

The first pattern generation module 241 of the processing device 200 may generate a motion pattern from the motion signal in operation S620. The motion pattern may be generated by using a lowpass filter and an adaptive filter. The motion pattern may also be generated by using various other methods.

The first estimation module 242 may estimate the next point in time of motion occurrence from the motion pattern in operation S630. When estimating the next point in time of motion occurrence, the first estimation module 242 may use the motion peak cycle included in the motion pattern. For example, the first estimation module 242 may estimate the next point in time of motion occurrence based on the most recent point in time of motion occurrence, to which the most recent motion peak cycle is added. Alternatively, the first estimation module 242 may estimate the next point in time of motion occurrence as the most recent point in time of motion occurrence, to which an average of at least one motion peak cycle included in the motion pattern is added. In addition, the first estimation module 242 may estimate the next point in time of motion occurrence based on the most recent point in time of motion occurrence, to which a value of the at least one motion peak cycle which is adaptively filtered is added. Furthermore, the first estimation module 242 may estimate the next point in time of motion occurrence by using various other methods.

The bio-signal sensor 110 detects a bio-signal of the object body in operation S640. The bio-signal sensor 110 may include an electrode which may contact the object body. The detected bio-signal is applied to the processing device 200.

The second pattern generation module 243 of the processing device 200 may generate the bio-signal pattern by combining the attenuation factor with the bio-signal of the next point in time of motion occurrence in operation S650. Here, the attenuation factor is a factor which attenuates the motion signal of the object body and may be a signal smaller than the reference value (e.g., 1). Also, a width of the attenuation factor may be determined by using at least one section of motion occurrence included in the motion pattern. For example, the width of the attenuation factor may be equal to or smaller than the section of motion occurrence. When the second pattern generation module 243 generates the bio-signal pattern, general algorithms, such as lowpass filtering and high pass filtering, may be used.

It will be understood that the operations S610 through S650 may be repeatedly performed after the operation S650 is performed.

Figure 7:
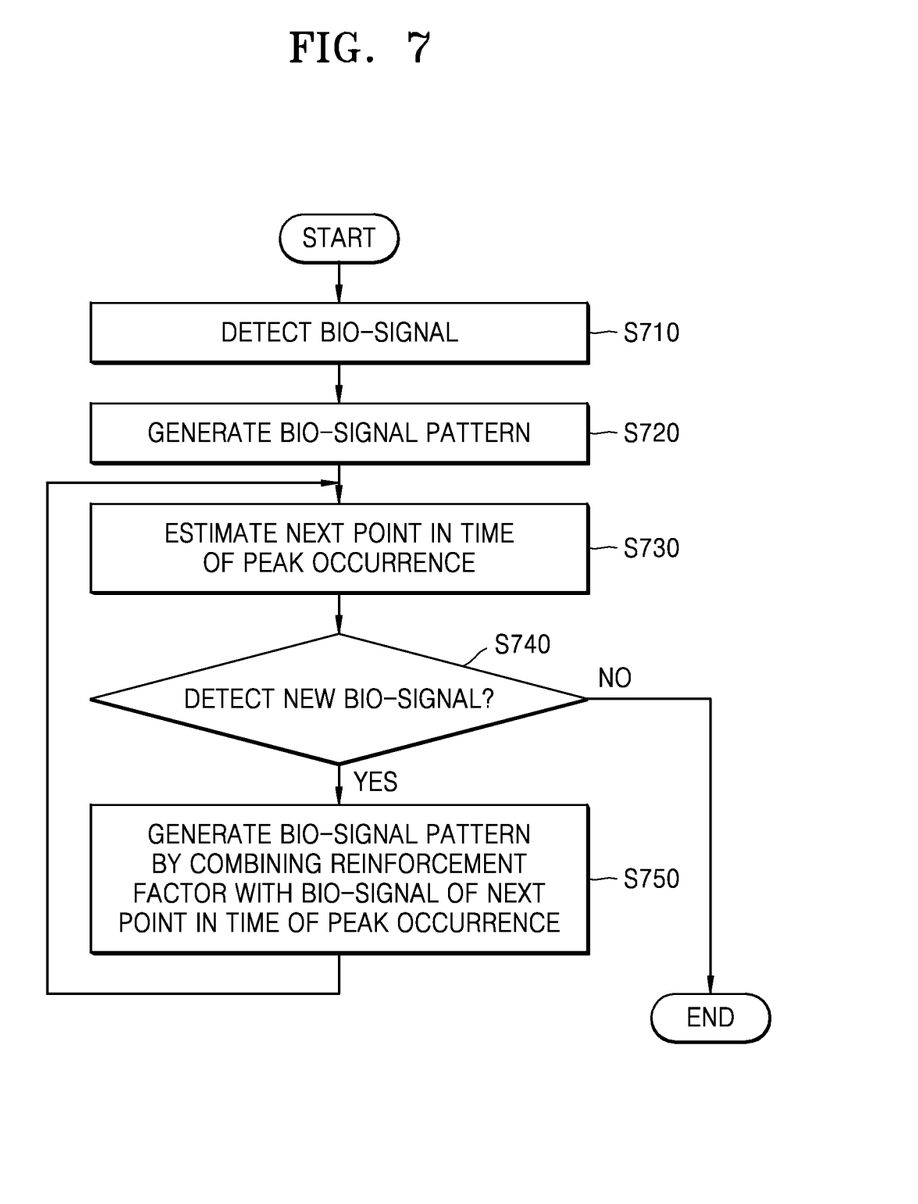
FIG. 7 is a flowchart illustrating a method of decreasing a motion artifact according to another exemplary embodiment.

FIG. 7 is a flowchart illustrating a method of decreasing a motion artifact, according to an exemplary embodiment.

The bio-signal sensor 110 detects a bio-signal of an object body in operation S710. The bio-signal sensor 110 may include an electrode which may contact the object body. The detected bio-signal is applied to the processing device 200.

The second pattern generation module 243 may generate the bio-signal pattern from the detected bio-signal in operation S720. The bio-signal pattern may be generated by using general algorithms which are applied to previous bio-signal patterns or by using the methods described in FIG. 5.

The second estimation module 244 may estimate the next point in time of peak occurrence from the bio-signal pattern in operation S730. When estimating the next point in time of peak occurrence, the second estimation module 244 may use the signal peak cycle included in the bio-signal pattern. For example, the second estimation module 244 may estimate the next point in time of peak occurrence based on the most recent point in time of peak occurrence, to which the most recent signal peak cycle is added. Alternatively, the second estimation module 244 may estimate the next point in time of peak occurrence based on the most recent point in time of peak occurrence, to which an average of at least one signal peak cycle included in the bio-signal pattern is added. In addition, the second estimation generation module 244 may estimate the next point in time of peak occurrence based on the most recent point in time of peak occurrence, to which a value of the at least one signal peak cycle which is adaptively filtered is added. Furthermore, the second estimation generation module 244 may estimate the next point in time of peak occurrence by using various other methods.

Also, when the bio-signal sensor 110 detects a new bio-signal and applies the new bio-signal to the processing device 200 in operation S740, the second pattern generation module 243 may combine the reinforcement factor to the bio-signal of the next point in time of peak occurrence to generate a new bio-signal pattern in operation S750. The reinforcement factor may be a factor which reinforces the bio-signal of the object body. For example, the reinforcement factor may be a signal larger than the reference value (e.g., 1). Also, a width of the reinforcement factor may be determined by using at least one section of peak occurrence included in the bio-signal pattern. For example, the width of the reinforcement factor may be equal to or smaller than the section of peak occurrence. The width and size of the reinforcement factor may vary according to bio-signals of object bodies, or may have predetermined values.

It will be understood that the operations S730 through S750 may be repeatedly performed after the operation S750 is performed.

Next, a method of decreasing a motion artifact will be described in detail with reference to signal wave forms according to an exemplary embodiment.

Figure 8A:
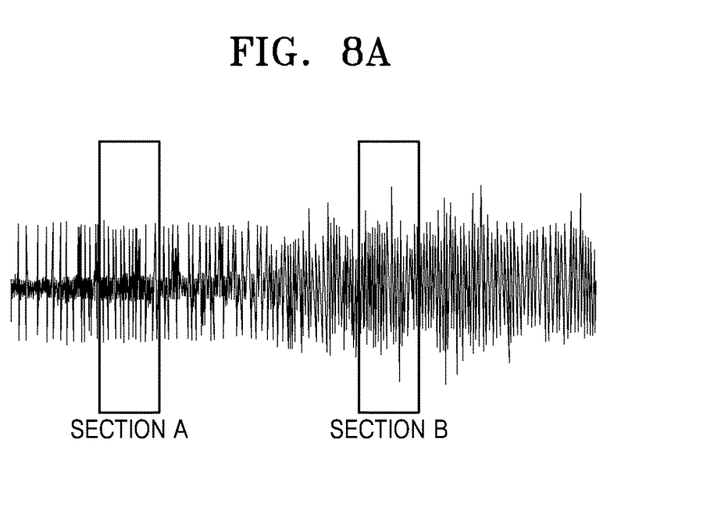
FIGS. 8A, 8B, and 8C show wave forms of an electrocardiogram (ECG) according to an influx of a motion artifact.
Figure 8B:
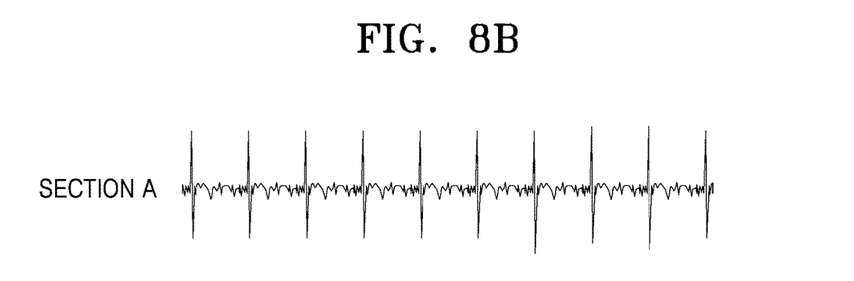
Figure 8C:
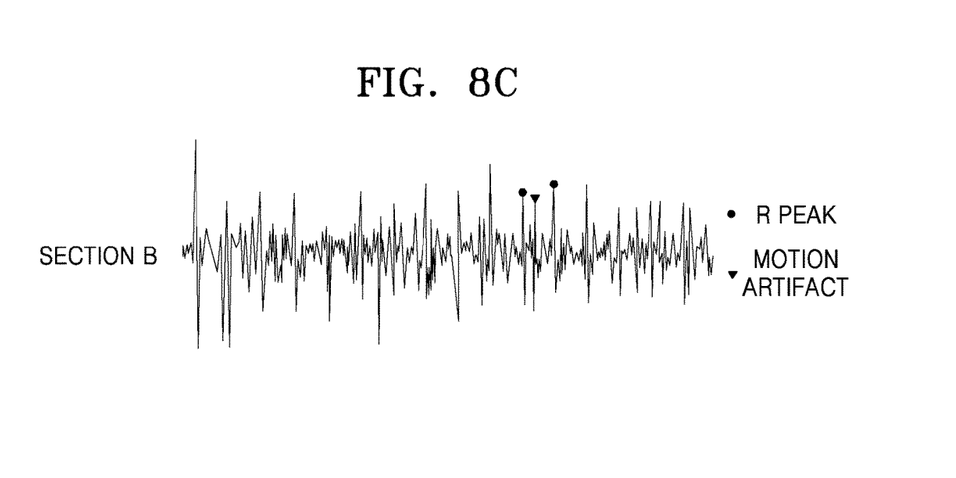

FIGS. 8A to 8C show wave forms of an electrocardiogram (ECG) according to an influx of a motion artifact. The wave form of the ECG of FIG. 8A may be obtained, for example, by measuring the object body during an exercise on a treadmill including walking, running up to a speed of 12 km/h, and again walking. In section A, which is a section of walking, effects of the motion artifact are not substantial, as shown in FIG. 8B. However, in section B, which is a section of running, many motion artifacts are present in the ECG wave form, as shown in FIG. 8C. The related art algorithm for measuring the ECG, that is, the related art algorithm which generates the bio-signal pattern, performs various preconditioning processes on a detected bio-signal, for example, removing noise of power lines, a base drift due to breath of the object body, and directional multi-gigabit (DMG) noise, by using a low pass filter and a high pass filter. After the preconditioning processes, the related art algorithm may detect an R peak by an adaptive thresholding method that uses an inclination, a size, and a width of the R-peak. However, as illustrated in FIG. 8C, when the motion artifact and the R peak have similar patterns, it may be difficult to detect to the R peak. This is because, in the preconditioning processes performed by the related art algorithm, a motion artifact in similar or substantially the same bandwidth as the ECG is not removed.

Figure 9:
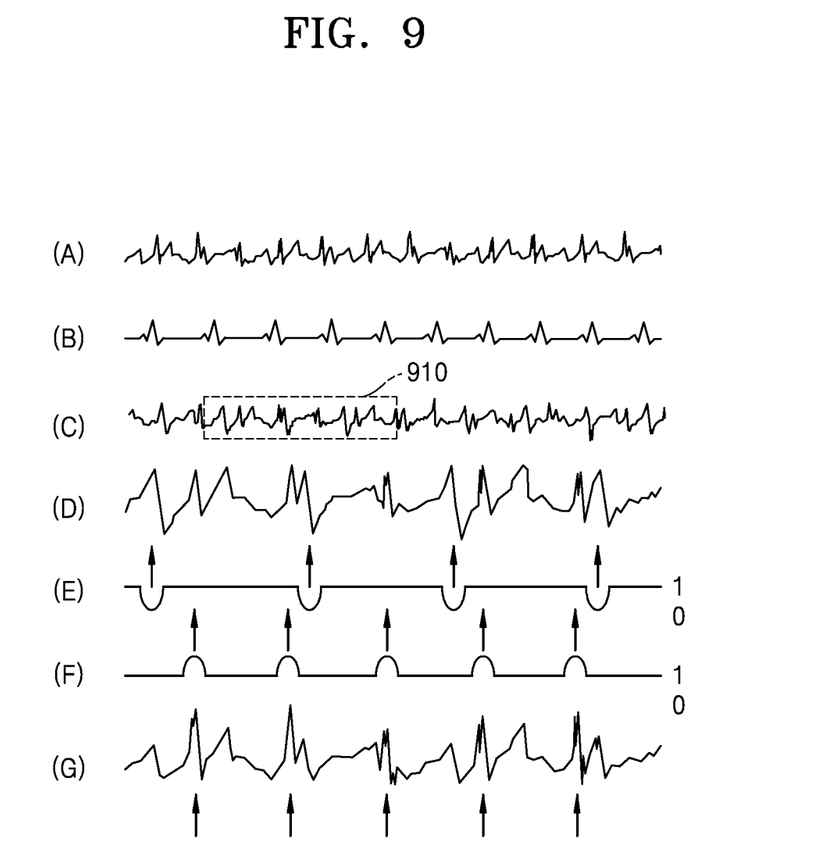
FIG. 9 is a view illustrating wave forms of a bio-signal to which an attenuation factor and a reinforcement factor are applied according to an exemplary embodiment.

FIG. 9 is a view illustrating wave forms of the bio-signal to which the attenuation factor and the reinforcement factor are applied according to an exemplary embodiment. Graph (A) shows an ECG signal measured when there is no motion of the object body. Graph (B) shows a motion signal which represents motion of the object body that is measured. Graph (C) shows an ECG signal measured when there is motion of the object body represented as the motion signal. Graph (D) shows an enlarged view of a portion 910 of the ECG signal of Graph (C). Graph (E) shows a pattern of the attenuation factor generated from the motion signal of Graph (B). Graph (F) shows a pattern of the reinforcement factor generated from the ECG signal. Graph (G) shows an ECG signal generated when the pattern of the attenuation factor of Graph (E) and the pattern of the reinforcement factor of Graph (F) are applied to the ECG signal including motion of Graph (D). It is shown that the motion artifact, that is, the motion signal, is decreased in the ECG signal of Graph (G).

The method of processing the bio-signal according to the exemplary embodiments may be written as computer programs and may be implemented in general-use digital computers that execute the programs using a computer readable recording medium. The computer readable code can be recorded and/or transferred on a medium in a variety of ways, with examples of the medium including recording media, such as magnetic storage media (e.g., ROM, floppy disks, hard disks, etc.) and optical recording media (e.g., compact disc read only memories (CD-ROMs), or digital versatile discs (DVDs)).

As described above, according to one or more of the above exemplary embodiments, the next point in time of motion occurrence may be estimated and the factor for attenuating the motion occurrence may be applied, and thus, the motion artifact may be decreased.

Also, the next point in time of peak occurrence of the bio-signal may be estimated and the size of the peak may be enlarged by applying the factor for reinforcing the peak, and thus, the peak detection may become easy.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art.

What is claimed is:

1. A method of processing a bio-signal, performed by a bio-signal processing apparatus including at least one processor, the method comprising:

receiving, by a communication module, a motion signal of an object body from a motion sensor detecting motion of the object body at a first time, the motion signal comprising a plurality of motion occurrences, each of the plurality of motion occurrences corresponding to one motion peak;

generating, by the at least one processor, a motion pattern, including a current motion occurrence with respect to the first time, based on the motion signal of the object body, the motion pattern comprising a motion peak cycle, which is defined as a time interval between two neighboring motion peaks of motion occurrences, among the plurality of motion occurrences;

estimating, by the at least one processor, a point in time of a next motion occurrence from the motion pattern, the estimated point in time of the next motion occurrence being later than the first time;

determining, by the at least one processor, an attenuation factor, to be applied to a bio-signal of the object body at the estimated point in time of the next motion occurrence, a signal width of the attenuation factor being equal to or smaller than a section of a time interval of a most recent motion peak cycle corresponding to two neighboring motion peaks of the current motion occurrence and an immediately preceding motion occurrence, a size of the attenuation factor being equal to or greater than 0 and less than 1;

receiving, by the communication module, the bio-signal of the object body from a bio-signal sensor detecting the bio-signal at a second time, the second time being later than the first time; and generating, by the at least one processor, a bio-signal pattern by applying the attenuation factor, having the signal width equal to or smaller than the section of the time interval of the most recent motion peak cycle and having the size being equal to or greater than 0 and less than 1, to the bio-signal of the object body at the estimated point in time of the next motion occurrence, to reduce amplitude of the motion signal in a first section of the bio-signal.

2. The method of claim 1, wherein the estimating comprises estimating, by the at least one processor, the point in time of the next motion occurrence by using the time interval of the most recent motion peak cycle comprised in the motion pattern.

3. The method of claim 2, wherein the point in time of the next motion occurrence is estimated by adding the time interval of the most recent motion peak cycle to a most recent point in time of the current motion occurrence.

4. The method of claim 1, wherein the point in time of the next motion occurrence is estimated by adding an average of time intervals of motion peak cycles, included in the motion pattern, to a most recent point in time of the current motion occurrence.

5. The method of claim 2, wherein the point in time of the next motion occurrence is estimated by adding the time interval of the motion peak cycle, the motion peak cycle being adaptively filtered, to a most recent point in time of the current motion occurrence.

6. The method of claim 1, wherein the attenuation factor comprises a value smaller than a reference value.

7. The method of claim 1, further comprising estimating, by the at least one processor, a point in time of a next peak occurrence of the bio-signal from a current bio-signal pattern, wherein the generating the bio-signal pattern comprises applying a reinforcement factor to the bio-signal of the object body at the estimated point in time of the next peak occurrence, to increase amplitude of a second section of the bio-signal.

8. The method of claim 7, wherein the point in time of the next peak occurrence is estimated by using a time interval of a signal peak cycle comprised in the current bio-signal pattern.

9. The method of claim 8, wherein the point in time of the next peak occurrence is estimated by adding a time interval of a most recent signal peak cycle to a most recent point in time of a current peak occurrence of the bio-signal.

10. The method of claim 8, wherein the point in time of the next peak occurrence is estimated by adding the time interval of the signal peak cycle, the signal peak cycle being adaptively filtered, to a most recent point of a current peak occurrence of the bio-signal.

11. The method of claim 7, wherein the reinforcement factor is a signal larger than a reference value.

12. The method of claim 11, wherein the reference value is 1, and a signal width of the reinforcement factor is determined by using at least one section of a current peak occurrence included in the current bio-signal pattern.

13. The method of claim 1, wherein the bio-signal comprises an electrocardiogram (ECG) signal.

14. A method of processing a bio-signal, performed by a bio-signal processing apparatus including at least one processor, the method comprising:

receiving a bio-signal of an object body from a bio-signal sensor detecting the bio-signal of the object body at a first time;

generating, by the at least one processor, a bio-signal pattern based on the bio-signal of the object body, the bio-signal pattern comprising a plurality of peak occurrences, including a current peak occurrence with respect to the first time, each of the plurality of peak occurrences corresponding to one signal peak, the bio-signal pattern further comprising a signal peak cycle, which is defined as a time interval between two neighboring signal peaks of peak occurrences, among the plurality of peak occurrences;

estimating, by the at least one processor, a point in time of a next peak occurrence of the bio-signal from the bio-signal pattern, the estimated point in time of the next peak occurrence being later than the first time;

determining, by the at least one processor, a reinforcement factor, to be applied to a new bio-signal of the object body at the estimated point in time of the next peak occurrence, a signal width of the reinforcement factor being equal to or smaller than a time interval of a most recent signal peak cycle corresponding to two neighboring signal peaks of the current peak occurrence and an immediately preceding peak occurrence; and generating, by the at least one processor, a new bio-signal pattern by applying the reinforcement factor having the signal width determined based on the current peak occurrence to the new bio-signal at the point in time of the next peak occurrence, to increase amplitude of a section of the new bio-signal.

15. An apparatus for processing a bio-signal, the apparatus comprising:

a communicator configured to receive a motion signal of an object body from a motion sensor detecting motion of the object body at a first time, and to receive a bio-signal of the object body from a bio-signal sensor detecting the bio-signal at a second time, the second time being later than the first time, the motion signal comprising a plurality of motion occurrences and each of the plurality of motion occurrences corresponding to one motion peak; and a processor configured to:

generate a motion pattern, including a current motion occurrence with respect to the first time, based on the motion signal of the object body, the motion pattern comprising a motion peak cycle, which is defined as a time interval between two neighboring motion peaks of motion occurrences, among the plurality of motion occurrences, estimate a point in time of a next motion occurrence from the motion pattern, the estimated point in time of the next motion occurrence being later than the first time, determine an attenuation factor of which a signal width is equal to or smaller than an interval of the current motion occurrence included in the motion pattern, and generate a bio-signal pattern by applying the attenuation factor having the signal width determined based on the current motion occurrence to the bio-signal at the point in time of the next motion occurrence, to reduce amplitude of the motion signal in a first section of the bio-signal.

16. The apparatus of claim 15, wherein the processor is configured to estimate the point in time of the next motion occurrence by using a time interval of the motion peak cycle comprised in the motion pattern.

17. The apparatus of claim 15, wherein the processor is configured to estimate a point in time of a next peak occurrence of the bio-signal from a current bio-signal pattern, and apply a reinforcement factor to the bio-signal at the estimated point in time of the next peak occurrence, to generate the bio-signal pattern, to increase amplitude of a second section of the bio-signal.

18. The apparatus of claim 17, wherein the processor is configured to estimate the point in time of the next peak occurrence by using a time interval of a signal peak cycle of the bio-signal comprised in the current bio-signal pattern.

* * * * *